United States Patent
Brasch (12)

(10) Patent No.: US 6,203,778 B1
(45) Date of Patent: Mar. 20, 2001

(54) PARTICULATE RADIOPAQUE CONTRAST AGENT FOR DIAGNOSTIC IMAGING AND MICROVASCULAR CHARACTERIZATION

(75) Inventor: Robert C. Brasch, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/208,599

(22) Filed: Dec. 8, 1998

(51) Int. Cl.$^7$ .................................................... A61K 49/04
(52) U.S. Cl. ..................... 424/9.411; 424/9.42; 424/9.43; 424/9.44
(58) Field of Search ............................... 424/9.411, 9.42, 424/9.43, 9.44

(56) References Cited

U.S. PATENT DOCUMENTS

| | | | |
|---|---|---|---|
| 4,124,705 | * 11/1978 | Rothman et al. | 424/1.11 |
| 4,680,171 | 7/1987 | Shell et al. . | |
| 4,709,703 | * 12/1987 | Lazarow et al. | 600/431 |
| 4,861,580 | * 8/1989 | Janoff et al. | 424/1.21 |
| 4,888,248 | * 12/1989 | Hirai et al. | 424/1.29 |
| 4,948,739 | 8/1990 | Charmot . | |
| 5,019,370 | 5/1991 | Jay et al. . | |
| 5,233,995 | * 8/1993 | Yudelson et al. | 600/458 |
| 5,318,767 | 6/1994 | Liversidge et al. . | |
| 5,342,609 | 8/1994 | Meeh et al. . | |
| 5,358,702 | * 10/1994 | Unger | 424/9.322 |
| 5,407,659 | 4/1995 | Deutsch et al. . | |
| 5,419,892 | * 5/1995 | Cacheris et al. | 424/9.42 |
| 5,451,393 | 9/1995 | Liversidge et al. . | |
| 5,468,465 | 11/1995 | Deutsch et al. . | |
| 5,520,904 | * 5/1996 | Nosco et al. | 424/9.322 |
| 5,521,218 | 5/1996 | Osifo et al. . | |
| 5,543,133 | 8/1996 | Swanson et al. . | |
| 5,543,158 | 8/1996 | Gref et al. . | |
| 5,676,928 | 10/1997 | Klaveness et al. . | |
| 5,686,061 | 11/1997 | Li et al. . | |
| 5,688,486 | * 11/1997 | Watson et al. | 424/1.65 |
| 5,746,998 | * 5/1998 | Torchilin et al. | 424/9.45 |
| 5,766,572 | 6/1998 | Hasegawa et al. . | |
| 6,010,681 | * 1/2000 | Margerum et al. | 424/9.35 |

OTHER PUBLICATIONS

Cochran et al., "Ninth Annual Congress on Industrial Health: Report of the Panel on Environmental Hygiene" *Arch. Ind. Hyg.* 1:637 (1950).

Fischer, H.W., "Improvement in Radiographic Contrast Media Through the Development of Colloidal of Particulate Media: an Analysis," *J. Theor. Biol.* 67:653–670 (1977).

Gazelle, et al., "Nanocrystalline Computed Tomography Contrast Agents for Blood–Pool and Liver–Spleen Imaging," *Invest. Radiol.* 29, Supplement 2:S286–S288 (1994).

Hirohashi S. et al., "Usefulness of superparamagnetic iron oxide particle (AMI–25) enhanced MR imaging for the diagnosis of liver tumors: comparison with contrast enhanced CT" *Nippon Igaku Gakkai Zasshi* 54(8):776–783 (1994).

Knisely et al., "Selective Phagocytosis I," I. Ket. kgl. Danske Vidensk. Selskab, Biol. Skrifter 4(7) (1948).

Mattrey, R.F., "Blood–Pool Contrast Media Are the Idea Agents for Computed Tomography" *Invest. Radiol.* 26 Suppl. 1:S55–S56 (1991).

Rubin et al., "Nanoparticulate Contrast Media: Blood–Pool and Liver–Spleen Imaging" *Invest. Radiol.* 29:Suppl. 2:S280–S283 (1994).

Violante, M.R., "Potential of Microparticles for Diagnostic Tracer Imaging" *Acta Radioloica.* Suppl. 374:153–156 (1990).

Violante, M.R., et al., "Particulate Contrast Media" *Invest. Radiol.* 15 Suppl. 6:S330–S334 (1980).

Violante, M.R., et al., "Particulate Suspensions as Contrast Media" Handbook of Experimental Pharmacology vol. 73, Radiocontrast Agents Ch. 13 1992.

\* cited by examiner

*Primary Examiner*—Gary E. Hollinden
(74) *Attorney, Agent, or Firm*—Townsend and Townsend and Crew LLP

(57) ABSTRACT

The properties of a tissue extracellular space, particularly the microvascular component of that space can be characterized by the use of x-ray diagnostic modalities in conjunction with particulate contrast agents. The present invention provides a method for characterizing a property of a tissue extravascular space utilizing radiopaque particulate contrast. Moreover, the present invention provides a novel class of particulate agents suitable for use in conjunction with the methods provided herein.

22 Claims, No Drawings

PARTICULATE RADIOPAQUE CONTRAST AGENT FOR DIAGNOSTIC IMAGING AND MICROVASCULAR CHARACTERIZATION

BACKGROUND OF THE INVENTION

X-ray imaging techniques, including radiography, fluoroscopy and computed tomography (CT) x-ray imaging are well known and extremely valuable tools for the detection and diagnosis of various disease states in the human body. In CT, the usual x-ray film image is replaced by sets of digitized matrices which represent the x-ray attenuation through the body. CT imaging allows 2-dimensional cross-sectional images of the body's organs and interior spaces to be acquired. In addition to its ability to produce cross-sectional images, CT imaging provides greater sensitivity to attenuation differences between tissues than conventional x-ray imaging. In spite of its sensitivity to attenuation differences, it is still quite common to perform CT imaging in conjunction with administering a radiopaque contrast agent.

Many different types of tissue and tumors can be imaged by CT imaging, including, but not limited to, brain, lungs, heart, and any solid tumor found in any soft tissue in the body (including liver, pancreas, ovaries, etc.). Contrast enhanced CT imaging can be used to enhance the visibility of vascular structures of in and around tumors, such as breast, lung, prostate, head and neck (squamous), rectal, testicular, bladder and ovarian carcinomas, soft tissue and central nervous system tumors.

Radiopaque contrast agents provide a means to vary image contrast and to improve the differentiation between pathological and physiological phenomena. An excellent background on contrast agents and media in medical imaging is provided by D. P. Swanson et al., PHARMACEUTICALS IN MEDICAL IMAGING, 1990, MacMillan Publishing Company, the disclosure of which is hereby incorporated by reference in its entirety. Briefly, in x-ray imaging techniques, transmitted radiation is used to produce an image or a series of images based upon overall tissue attenuation characteristics. X-rays pass through various tissues and are attenuated by scattering (i.e., reflection or refraction) or energy absorption. However, certain body organs, vessels and anatomical sites exhibit so little absorption of x-ray radiation that images of these body portions are difficult to obtain. To overcome this problem, radiologists routinely introduce an x-ray absorbing contrast medium into such body organs, vessels and anatomical sites.

Several classes of compounds have been explored as potential contrast agents. For CT, these classes include both small molecule and particulate contrast media. See, for example, Lin, "Radiopaques," In, KIRK-OTHMER ENCYCLOPEDIA OF CHEMICAL TECHNOLOGY, Volume 20, pp. 907–930, John Wiley and Sons, New York, 1996. There currently exist classes of small molecule radiographic contrast agents useful for a broad range of diagnostic techniques, including angiography, arteriography, aortography, ventriculography, venography, urography, myelography, cholecystography, cholangiography, gastointestinal radiography, arthography and hysterosalpingography. Currently available x-ray contrast agents generally exhibit a lack of site directed delivery or compartmentalization. Consequently, large quantities of agent are normally required for imaging. It is, therefore, desirable to restrict the contrast agent to specific biological or anatomical compartments, particularly the blood pool, liver, kidney or spleen. This would reduce the overall amount of agent administered to achieve the desired contrast enhancement.

When small molecular contrast agents are used, maximum enhancement of major blood vessels takes place during the so-called vascular phase of contrast medium kinetics which occurs within about the first two minutes following the intravascular infusion or bolus injection of the contrast medium. This is because the plasma concentration of an intravascular contrast medium decreases rapidly as a result of vascular mixing, transcapillary diffusion of the medium from the circulation into the interstitial spaces, and renal excretion. Consequently, imaging of blood vessels must take place within a narrow time window, typically within a few minutes after infusion or injection of the x-ray contrast agent.

Currently, there is no commercially available x-ray contrast agent for imaging blood vessels which provides good contrast images of the vasculature for an extended period of time. Therefore, multiple injections are often required to visualize the vasculature adequately. Furthermore, arteriography, as currently practiced, typically requires percutaneous or surgical catheterization, fluoroscopic localization and multiple bolus arterial administrations to adequately visualize a given vascular region.

Although certain particulate radiopaque contrast agents are known in the art, these have principally been used to achieve improved visualization of the liver, kidney and through accumulation of the agent by the mononuclear phagocyte system (MPS) of the reticuloendothelial system (RES). The operative design principle behind these agents is control of particle size and surface coating to ensure phagocytization.

Particles that are rapidly phagocytized by the MPS are typically greater than 100 nanometers in size. For example, See, Violante et al., *Acta Radiol Suppl.* 374: 153–156 (1990); and Rubin etal., *Invest Radiol.* Suppl 2: S280–S283 (1994). Another factor affecting the rate of phagocytization is the nature of the coating on the particle. For example, particles which do not acquire a serum protein coat, such as those coated with neutral dextran, healthy red cells and fat particles, are not phagocytized quickly, but remain longer in the blood pool. See, for example, U.S. Pat. No. 5,543,158, to Gref et al.; Knisely et al., *I. Det, kgl. Danske Vidensk. Selskab, Biol. Skrifter* 4: 1 (1948); and Violante and Fischer, "Particulate Suspensions as Contrast Media," in, Handbook of Experimental Pharmacology, Vol. 73, RADIOCONTRAST AGENTS, Chapter 13.

Recent reports from the field of magnetic resonance imaging (MRI) have demonstrated that contrast agents that remain largely confined to the intravascular space in healthy tissue (i.e., macromolecular contrast agents) can be used to detect areas of injury and/or disease. The underlying mechanism allowing this detection is the transit of a predominantly intravascular agent through a region of metabolically or structurally altered or diseased vasculature into the interstitium of the surrounding tissue. This passive diffusion into the interstitium results in a pooling of the contrast agent in the interstitium. This pooling is reflected in an increase in the contrast medium concentration in the tissue relative to the blood concentration over time. See, for example, Ogan et al., *Invest. Radiol.* 22: 665–671 (1987); van Dijke et al., *Radiology* 198: 813–818 (1996); Schwickert et al., *Radiology* 198: 893–898 (1996); and Cohen et al., *Invest. Radiol.* 29: 970–977 (1995). In spite of its potentially far-ranging utility, this technique has yet to be exploited in the field of x-ray, and particularly CT imaging.

A method which utilized CT imaging in conjunction with a radiopaque contrast agent that remained principally confined to the intravascular space in healthy tissue, but which pass across the endothelial membrane of abnormal vasculature and pool in the interstitium in altered or diseased tissue would provide a significant advance in the field of medical diagnostic imaging. Surprisingly, the present invention provides such a method.

SUMMARY OF THE INVENTION

Because the microvascular endothelium of tumors and injured tissues exhibits high permeability rates relative to normal tissue, particulate agents passively diffuse from the intravascular space into the extravascular interstitial compartments of these tissues. The poorly developed or absent lymphatic system of tumors and some tissues limits the rate of movement of particles out of these tissues. This combination (enhanced permeability and retention) is used during imaging of these tissues. The tumors and injured tissues are seen by imaging as a time-dependent increased signal intensity in the interstitial space. The prolonged retention of macromolecules and particles within the vascular and extravascular interstitial compartments of tumors and some injured tissues provides a unique opportunity to study the properties of these tissues and their vasculature.

The present invention provides a novel method of x-ray or CT imaging utilizing a particulate radiopaque agent that remains substantially confined to the intravascular space in healthy tissue.

In a first aspect, the present invention provides a method for determining a property of a tissue extracellular space comprising an intravascular space and an extravascular interstitial space, the method comprising:

(a) delivering to a tissue intravascular space a particulate radiopaque agent, wherein the agent is not substantially phagocytized by cells of the reticuloendothelial system during at least a selected time period;

(b) allowing the agent to distribute between the intravascular space and the extravascular interstitial space for the selected time period, thereby forming a distribution of the agent;

(c) measuring the distribution of the agent by obtaining at least one x-ray absorption data set; and (d) determining the property from the data set.

In a second aspect, the present invention provides a particulate radiopaque agent comprising:

(a) a radiopaque core, with the proviso that the core is not an iron oxide; and (b) an organic layer substantially surrounding the core.

In a third aspect, the present invention provides a pharmaceutical formulation comprising:

a radiopaque particle comprising:
  (a) a radiopaque core, with the proviso that the core is not an iron oxide;
  (b) an organic layer substantially surrounding the core; and
  (c) a pharmaceutically acceptable sterile carrier.

Other objects and advantages of the present invention will become apparent to those of skill in the art from a reading of the detailed description that follows.

DETAILED DESCRIPTION OF THE INVENTION AND THE PREFERRED EMBODIMENTS

Definitions

"Accumulation" of particulate contrast medium in the tissue interstitial space refers to the increasing concentration of particulate contrast medium leaked from the tissue microvasculature into the interstitial space of the tissue.

"Animal" refers to any vertebrate, preferably a mammal, including humans.

"Coefficient of permeability surface area product" (Kps) refers to a measurement of tissue vasculature permeability. "$K^{PS}$"$\approx$(PV)(FLR$_{in}$), where PV is the tissue plasma volume and FLR$_{in}$ is the fractional leak rate of a particulate contrast agent from the plasma into interstitial fluid of the tissue. $K^{PS}$ can also be determined from a computer assisted fit of the model to the data.

"Contrast media" refers to pharmacologically acceptable particulate x-ray opaque substances.

"Dynamic attenuation response" refers to a profile of x-ray attenuation values generated by multiple images demonstrating the change of attenuation over time.

"Ferrous" refers to iron in any oxidation state.

"Grading a tumor" refers to the process of determining whether a tumor is benign or malignant and if malignant, determining the degree of malignancy.

"Grey scale" and "Assigning a grey scale" refers to converting the data obtained from an image to a shade of grey. Typically, the greater the number, the paler the color or Grey value.

"Histopathologic grade of tumor" refers to the grade of a tumor given by a pathologist after microscopically examining a portion of the tumor.

"Imaging" refers to a method of examining tissue by exposing the tissue to incident x-ray energy and measuring the differences in absorption of the energy transmitted by or absorbed by the tissue.

"Interstitial space of a tissue" refers to the area between cells in a tissue exclusive of vascular spaces.

"Kinetic model" refers to a mathematical algorithm which, when data from the images over time are entered (fitted), determines the value of physiologic parameters including the microvascular permeability of the tumor.

"Linear regression analysis" refers to a method of estimating and setting confidence intervals for parameters involved in expressing a linear trend in a population. The basic assumptions underlying this method are: (1) the values of the independent variables are fixed; (2) $\mu_{Y|x}$=A+Bx; (3) for each x, the variance of the distribution of Y is the same and equal to $\sigma^2$; and (4) the random variables representing the response variable are independently distributed. After the parameters A, B, $\mu_{Y|x}$, and $\sigma^2$ are determined, confidence intervals for these parameters are determined and a hypothesis regarding these parameters is tested. Typically, the test is the null hypothesis, wherein B is equal to 0.

"Particulate contrast media" refers to particles which are substantially x-ray opaque and which have particle sizes of from about 10 angstroms to 1 micron in diameter.

"CT scanning" refers to a method of examining interior soft tissues in vivo. The subject is placed in an instrument having an x-ray source which projects an x-ray beam which is collimated to lie within an X-Y plane of a Cartesian coordinate system. The x-ray beam passes through the object being imaged, such as a patient and impinges on an array of radiation detectors. The intensity of the transmitted radiation is dependent upon the attenuation of the x-ray beam by the object.

"Microvascular permeability" refers to the ability of a tracer of a selected size to traverse the endothelial barrier of microvessels. It has been established that the microvessels of tumors, diseased and traumatized tissue are particularly "leaky" with permeability being high compared to the microvessel of non-tumorous, healthy and intact tissues.

"Non-magnetic" characterizes materials that are not paramagnetic, superparamagnetic or ferromagnetic.

"Pixel" refers to the smallest region of interest that can be examined and individually processed in a visual display system.

"Radiopaque" refers to a substance that absorbs or deflects a substantial proportion of incident x-ray photons, typically by photoelectronic effects or Compton scattering.

"Region of interest (ROI)" refers to the area within an image determined for analysis.

"Scarff-Bloom-Richardson histological grading of tumors" refers to determining the quantitated grade of a malignancy based on three criteria: (1) the pleomorphism of the nucleus; (2) the mitotic index; and (3) ductoglandular formation.

"Signal intensity" refers to the brightness of imaged tissue. The brighter the tissue, the higher the signal intensity.

"Standard curve of permeability values" refers to a statistically significant standard curve of microvascular permeability values versus grade of tumors. It is generated by comparing the microvascular permeability values obtained for tumors and comparing them to the histopathological grade of the tumor.

"Tumor" refers to a mass of benign or malignant cells including the central mass and the tumor rim. The tumor rim is the edge of the tumor where the tumor cells are most likely to be alive and dividing. The center of a solid tumor can be a necrotic mass of cells and therefore grading of the central tumor mass may not be indicative of the malignancy of the tumor at the time the tumor is graded.

Methods for Determining a Tissue Property

The present invention provides a novel method of x-ray or CT imaging utilizing a particulate radiopaque agent that remains substantially confined to the intravascular space in healthy tissue.

Thus, in a first aspect, the present invention provides a method for determining a property of a tissue extracellular space comprising an intravascular space and an extravascular interstitial space, the method comprising:

(a) delivering to a tissue intravascular space a particulate radiopaque agent, wherein the agent is not substantially phagocytized by cells of the reticuloendothelial system during at least a selected time period;

(b) allowing the agent to distribute between the intravascular space and the extravascular interstitial space for the selected time period, thereby forming a distribution of the agent;

(c) measuring the distribution of the agent by obtaining at least one x-ray absorption data set; and (d) determining the property from the data set.

In presently preferred embodiments, the method of the invention further comprises measuring a series of x-ray absorption data sets of the tissue vascular space over a time period comprising the selected time period. The intravascular data set can serve as a baseline, allowing tissue properties characterized by deviation from this baseline to be determined.

The data acquired from the absorption data sets is preferably processed by a method comprising at least one algorithm that allows the property of the tissue to be determined. In a preferred embodiment, serial x-ray absorption data sets are acquired over a time period of from about 10 seconds postcontrast to about 5 hours postcontrast, more preferably from about 30 seconds postcontrast to about 1 hour postcontrast, still more preferably from about 1 minute postcontrast to about 10 minutes postcontrast. As used herein, "postcontrast" refers to that time period following the administration of the contrast agent to the subject.

Utilizing the method of the invention, a wealth of information can be obtained regarding the microvascular characteristics of a range of tissues of interest. The tissue is preferably a member selected from the group consisting of normal tissue, diseased tissue, traumatized tissue and combinations thereof. When the tissue is diseased or injured, the tissue is preferably a member selected from the group consisting of tissues which are neoplastic, malignant, hyperplastic, dysplastic, arthritic, ischemic, inflamed, injured, infected, healing and combinations thereof.

In a preferred embodiment the property of interest is a tissue vascular volume. In another preferred embodiment, the property is a microvascular permeability. In a further preferred embodiment, the intravascular space and the extravascular interstitial space are joined communicatively and the property is a rate of transfer of the particulate agent from the intravascular space into the extravascular space.

Although any appropriately sized radiopaque agent known in the art or later discovered can be used to practice the present invention, in a preferred embodiment, the particulate agent is nonferrous. Preferred particle sizes are from about 1 nanometers to about 1 micron in diameter, more preferably from about 5 nanometers to about 500 nanometers in diameter, still more preferably from about 10 nanometers to about 60 nanometers in diameter.

In certain preferred embodiments, the agent is a member selected from the group consisting of liposomes, emulsions, inorganic particles, organic particle, mixed organic-inorganic particles and combinations thereof.

Although any radiopaque core material can be used to practice the instant invention, certain materials are presently preferred. Thus, in one preferred embodiment, the method utilizes particles wherein the agent comprises an organic iodinated radiopaque agent. In another preferred embodiment, the method utilizes a particle comprising an inorganic core substantially surrounded by an organic coating. In still further preferred embodiments, the core is a metal in its (0) oxidation state. In yet another preferred embodiment, the inorganic core is cesium iodide (CsI).

The method of the invention can be practiced with particles having substantially any biocompatible organic coating. In preferred embodiments, the organic coating prevents the rapid phagocytization of the particles by the RES of the subject. In these embodiments, preferred coatings include, for example, polysaccharides, polyethers and combinations thereof. In still further preferred embodiments, the organic coating is, for example, a poly(ethyleneglycol), sialic acid, glucouronic acid, dextran, hydroxyethylstarch and combinations thereof. Suitable particles are discussed in greater detail below.

Particulate Agents

In a second aspect, the present invention provides a particulate radiopaque agent comprising:

(a) a radiopaque core, with the proviso that the core is not an iron oxide; and (b) an organic layer substantially surrounding the core.

In preferred embodiments, the core is an organic, preferably iodinated contrast agent. In other preferred embodiments, the core is an inorganic iodide such as cesium iodide or, alternatively a metal in its (0) oxidation state. Presently preferred metals include, Cu(0), Ni(0), Pd(0), Pt(0), Au(0), Ag(0) and combinations thereof. The metal can be magnetically active (e.g., paramagnetic, superparamagnetic, etc.), however, in preferred embodiments, the metal core is not superparamagnetic.

Preferred organic coatings are those which will enable the particle to escape rapid phagotization by the RES of the subject. Suitable organic coatings include poly(ethyleneglycol), glucouronic acid, sialic acid, combinations of these groups and polymers of one or more than one of these groups. When polymers of these groups are utilized, they can be copolymers formed between these and other groups.

A wide range of particulate compounds of different sizes and compositions are appropriate for use in conjunction with the present invention. One of skill in the art will be able to choose among the variety of available particles to practice the present invention without resort to undue experimentation. In a preferred embodiment, the particles of use in the present invention include liposomes, emulsions, inorganic particles, organic particles, mixed inorganic-organic particles and combinations thereof.

Although particles of a wide range of sizes can be used in the present invention, certain particle sizes are presently preferred. Thus, in a preferred embodiment, the selected particle size is from about 1 nanometers to about 1 microns in diameter, more preferably from about 5 nanometers to about 500 nanometers in diameter, more preferably still, from about 10 nanometers to about 60 nanometers in diameter.

In a currently preferred embodiment, the particles are made from a radiopaque organic material. The particles are preferably sparingly soluble or insoluble in water. Exemplary compounds include, but are not limited to, esters and other water insoluble derivatives of diatrizoic acid, iothalamic acid, urokinec acid and metrizoic acid formulated as nanoparticles. In another preferred embodiment, the radiopaque agent is an inorganic iodide, such as cesium iodide. In yet another preferred embodiment, the radiopaque material is a particle of a metal in its (0) oxidation state. In each of these embodiments, after formulation of the particulate cores, the cores are generally coated with an organic moiety including hydrophilic polymers such as a poly(ethyleneglycol), dextran or carboxymethyldextran. Alternatively, the core is encapsulated into a liposome.

Methods of making finely divided particles of drugs and drug carriers are well known in the art and the size and size range of such particles in pharmaceutical compositions can be closely controlled. For example, dry milling techniques have been used to reduce particle size and hence influence drug absorption. In conventional dry milling, as discussed by Lachman, et al., The Theory and Practice of Industrial Pharmacy, Chapter 2, "Milling", p.45 (1986), the limit of fineness is reached in the region of 10 $\mu$m. Commercial airjet milling techniques have provided particles ranging in average particle size from as low as about 1 $\mu$m to 50 $\mu$m.

EPO 275,796 describes the production of colloidally dispersible systems comprising a substance in the form of spherical particles smaller than 500 nm. This patent describes a method involving a precipitation effected by mixing a solution of the substance and a miscible non-solvent for the substance and results in the formation of non-crystalline nanoparticles.

U.S. Pat. No. 4,107,288 describes particles in the size range from 10 to 1,000 nm containing a biologically or pharmacodynamically active material. These particles comprise a crosslinked matrix of macromolecules having the active material supported on or incorporated into the matrix.

U.S. Pat. No. 5,145,684 discloses a process for preparing particles consisting of a crystalline drug substance having a surface modifier or surface active agent adsorbed on the surface of the particles in an amount sufficient to maintain an average particle size of less than about 400 nanometers. The process of preparation comprises the steps of dispersing the drug substance in a liquid dispersion medium and applying mechanical means in the presence of grinding media to reduce the particle size of the drug substance to an average particle size of less than 400 nm. The particle size can be reduced in the presence of a surface active agent. The presence of the surface active agent prevents flocculation/agglomeration of the nanoparticles.

In another preferred embodiment, the particulate cores of the agents are prepared by microfluidization. Microfluidizers have been utilized for preparing small particle-size materials in general. Microfluidizers are relatively new devices operating on the submerged jet principle. In operating a microfluidizer to obtain nanoparticulates, a premix flow is forced by a high pressure pump through a so-called interaction chamber consisting of a system of channels in a ceramic block which split the premix into two streams. Precisely controlled shear, turbulent and cavitational forces are generated within the interaction chamber during microfluidization. The two streams are recombined at high velocity to produce droplet shear. The so-obtained product can be recycled into the microfluidizer to obtain smaller and smaller particles.

At least two distinct advantages of microfluidization over conventional milling processes have been reported, including substantial reduction of contamination of the final product and the ease of production scaleup.

In a preferred embodiment, the radiopaque material is loaded into a liposome. Liposomes encapsulating radiopaque contrast agents can be prepared using routine techniques. Liposomes can easily be prepared in sizes ranging approximately 20 nanometers to approximately 1000 nanometers. Presently preferred liposomes are small unilamellar vesicles of from about 20 nanometers to about 100 nanometers in diameter.

In an exemplary embodiment, the liposome is prepared by simple hydration of the lipid constituents in an aqueous milieu in which the radiopaque agent is dissolved or suspended. Generally, mechanical agitation is provided by a vortex mixer. Once liposomes are prepared, they can be mechanically broken. The broken liposomes reform closed vesicles having smaller sizes and lamellar number. Thus, it is well-known in the art to prepare single unilamellar liposomes from multilamellar liposomes by sonication or a French press. Moreover, homogeneous sized liposomes can be produced by extrusion through a membrane with uniform pore sizes. For example, a formulation of 10 nanometer liposomes can be prepared by extruding a mixture of liposomes of varying sizes through a polycarbonate membrane having 10 nanometer pores.

Liposomal drug delivery systems have been extensively studied for the intravenous administration of biologically active materials, because they were expected to freely circulate in the blood. It was found, however, that liposomes are quickly cleared from the blood by uptake through the reticuloendothelial system. The coating of liposomes with poly(ethyleneglycol) increases their half life substantially. The flexible and relatively hydrophilic PEG chains apparently induce a steric effect at the surface of the liposome that reduces protein adsorption and thus RES uptake. T. M. Allen, C. Hansen, *Biochimica et Biophysica Acta,* 1068: 133–141 (1991); T. M. Allen, et al., Biochimica et Biophysica Acta, 1066: 29–36 (1991); V. Torchilin, A. Klibanov, "The Antibody-linked Chelating Polymers for Nuclear Therapy and Diagnostics", Critical Reviews in Therapeutic Drug Carrier Systems, 7(4): 275–307 (1991); Maruyama, et al., *Chem. Pharm. Bull.,* 39(6): 1620–1622 (1991); Woodle, et al., *Biochimica et Biopbysica Acta;*

193–200 (1992); and Lassic, et al., *Biochimica et Biophysica Acta*, 1070: 187–192 (1991); and A. Klibanov, et al., *Biochimica et Biophysica Acta*, 1062: 142–148 (1991).

In a particularly preferred embodiment, the liposomes are small unilamellar vesicles that are modified on their surface with a material that retards scavenging of the liposomes by the RES. Liposomes that avoid the RES are known in the art. These so-called "stealth" RES avoiding liposomes have been prepared by modifying the liposome surface with sialic acid, glucouronic acid or poly(ethyleneglycol). See, for example Gabizon et al., Proc. Natl. Acad. Sci. USA., 85: 6949 (1988); Blume et al., Biochim. Biophys. Acta, *1029:* 91 (1990); Scherphofet al., Biochem. J., 221: 423 (1984); Klibanov et al., FEBS Lett., 268: 235 (1990).

Many other particle types useful in practicing the present invention will be apparent to those of skill in the art and the practice of the method of the invention is not limited to specific particle structures or compositions. Those of skill in the art have access to numerous publications and patents that have been devoted to emulsions, liposomes and/or microencapsulated suspensions of various substances including drug substances produced by the use of microfluidizers. The following list is intended to be illustrative and not limiting. See, for example:

1) U.S. Pat. No. 5,342,609, directed to methods of preparing solid apatite particles used in magnetic resonance imaging, x-ray and ultrasound;
2) U.S. Pat. No. 5,228,905, directed to producing an oil-in-water dispersion for coating a porous substrate, such as wood;
3) U.S. Pat. No. 5,039,527 is drawn to a process of producing hexamethylmelamine containing parenteral emulsions;
4) U.S. Pat No. 5,543,133 is drawn to a process for preparing x-ray contrast compositions comprising nanoparticles;
5) Gregoriadis et al., "A Procedure for the Efficient Entrapment of Drugs in Dehydration-Rehydration Liposomes (DRVs)," *Int. J Pharm.* 65: 235–242 (1990);
6) Doegito et al., "New Techniques for Preparing Submicronic Emulsions-Application to Amphotericine-B,: *STP Pharma Sciences* 4: 155–162 (1994);
7) Lidgate et al., "Formulation of Vaccine Adjuvant Muramyldipeptides. Part 3. Processing Optimization, Characterization and Bioactivity of an Emulsion Vehicle," *Pharm Res.* 6: 748–752 (1989);
8) Talsma et al., "The Size Reduction of Liposomes with a High Pressure Homogenizer (Microfluidizer): Characterization of Prepared Dispersions and Comparison with Conventional Methods," *Drug Dev. Ind. Pharm.* 15: 197–207 (1989);
9) Lidgate et al., "Sterile Filtration of a Parenteral Emulsion," *Pharm. Res.* 9: 860–863 (1990);
10) Bodmeier et al., "Indomethacin Polymeric Nanosuspensions Prepared by Microfluidization," *J Contr. Rel.* 12: 223–233 (1990);
11) Bodmeier et al., "Spontaneous Formation of Drug-Containing Acrylic Nanoparticles," *J Microencap*, 8: 161–170 (1991); and
12) Koosha et al., "Nanoparticle Production by Microfluidization," *Archiv Der Pharmazie* 321: 680 (1988).

The methods disclosed in each of these publications are broadly applicable to the preparation of particles useful in practicing the method of the invention.

In another preferred embodiment, the particle comprises an inorganic core surrounded by a hydrophilic organic coating. Any inorganic particle that is substantially radiopaque is useful in practicing the present invention. One of skill in the art can readily assess the radiopacity of a given particle using art-recognized methods such as x-ray densitometry and, thus, choose an appropriate inorganic core size and material.

Useful radiopaque cores include species such as iodide salts of metal ions and metal particles in their (0) oxidation state. In a presently preferred embodiment, the inorganic core is a cesium iodide core. Cesium iodide is an attractive choice because of its x-ray opacity and acceptably low toxicity. See, for example, Cochran et al., *Arch. Ind. Hyg.* 1: 637 (1950).

Particles comprising a cesium iodide core can be prepared by a number of methods. In an exemplary embodiment, the cesium iodide core is fabricated in an appropriate size by methods such as milling, microfluidization, crystallization, precipitation and the like. In one embodiment, the cesium iodide core is then electrolessly plated with a thin layer of a metal such as Au(0) or Ag(0). Following the deposition of the metal film, the particle can be surface coated with a hydrophilic polymer such as poly(ethyleneglycol) as is explained in detail below. Methods of electrolessly plating metals onto inorganic cores are known to those of skill in the art. See, for example, U.S. Pat. No. 5,196,267, issued to Barder et al., on Mar. 3, 1993. Using this and similar methods, particles of the invention can be produced by providing inorganic core particles with thin layers, often monolayers, of a metal. Because the metal can be electrolessly plated in an alcohol solution, the water solubility of cesium salts is not a concern.

In another preferred embodiment, the inorganic core is selected from Au(0), Ag(0), Cu(0), Ni(0) and the like. Methods for preparing small particles of metals are known in the art and particles with a wide range of sizes can be produced using these methods. See, for example U.S. Pat. No. 4,252,677, issued to Smith, on Feb. 24, 1981, which describes the preparation of transition metal colloids with particles having diameters of from about 10 Angstroms to about 200 Angstroms. See, also, U.S. Pat. No. 5,609,907, issued to Natan, on Mar. 11, 1997, which describes the preparation of Au(0) and Ag(0) colloids having diameters of from about 3 nanometers to about 100 nanometers. Both of these disclosures are incorporated herein by reference.

In preferred embodiments, the inorganic core is substantially surrounded by an organic layer. The organic layer serves to protect the particle from rapid phagocytization by the Kupfer cells of the reticuloendothelial system and uptake by other metabolic systems within the body. Thus, the organic layer prolongs the intravascular half-life of the particles.

Many organic coatings appropos to particles of use in the present invention are known to those of skill in the art. The method of the present invention encompasses the use of particles utilizing a wide range of organic coating materials. In a preferred embodiment, the organic coating comprises a material is selected from polysaccharide and poly (ethyleneglycol) moieties.

The use of coatings which shield particulate agents from uptake by different systems in vivo is well known in the art. For example, a number of particulate injectable drug delivery systems have been investigated, including microcapsules, microparticles, liposomes and emulsions. A significant obstacle to the use of these injectable particulate materials in the present invention is the rapid clearance of the materials from the blood stream by the macrophages of the reticuloendothelial system (RES). For example, polystyrene particles as small as sixty nanometers in diameter are cleared from the blood within two to three minutes. By coating these particles with block copolymers based on poly(ethyleneglycol) and poly(propylene glycol), their halflives were significantly increased. See, Illum et al., *FEBSLett.*, 167: 79 (1984).

Colloidal metals are known in the art and are utilized as treatments for rheumatoid arthritis, malignancy, and as nutritional supplements. See, for example, Yarom et al. *Arch Pathol* 99(1):36–42 (1975). The attractive toxicological profiles of colloidal metals such as gold and silver makes them an appropriate choice for a particulate core. Additionally, hydrophilic polymers such as poly(ethyleneglycol) are approved for clinical use as well. Thus, a gold particle coated with poly(ethyleneglycol) might be an excellent candidate for advancement to the clinic. Additionally, these materials are commercially available with particle sizes ranging from 2 nanometers to 40 nanometers (SPI Supplies, West Chester, Pa.).

Thus, in a presently preferred embodiment, the particles of the invention comprise an Au(0) or Ag(0) core that has been coated with a poly(ethyleneglycol) coating. Although a range of preparative methods can be used to produce such particles, in a preferred embodiment, the metal core is contacted with a poly(ethyleneglycol) thiol. These thiols can be prepared in a number of molecular weights (Zalipsky et al., *Int. J Peptide Protein Res.* 30: 740 (1987)) and are also commercially available (Shearwater Polymers, Huntsville, Ala.).

In a typical procedure, the particles will be contacted with an ethanolic solution of the glycol thiol. The derivatized particles will then be purified by, for example filtration and washing repeatedly with ethanol and/or water. The particles can then be resuspended into a sterile vehicle such as normal saline prior to administering them to the subject. To ensure elimination from the body, the poly(ethyleneglycol) should have a molecular weight of approximately 20,000 Daltons or less.

In addition to poly(ethyleneglycol), there are a number of specific surface coatings which can be used to construct particles which are of use in the method of the invention. These include, for example, a diblock, triblock, or multiblock copolymer of poly(alkyleneglycol) with poly(lactic-co-glycolic acid). Another useful coating comprises a copolymer of poly(alkyleneglycol) with a polyanhydride, polyhydroxybutyric acid, polyorthoesters other than the homopolymer of lactic acid, polysiloxanes, polycaprolactone, or copolymers prepared from the monomers of these polymers, wherein the copolymer can be of diblock, triblock, or multiblock structure. Alternatively, the injectable particle can include a surface which is a copolymer of the form poly(alkyleneglycol)-[poly(lactic-co-glycolic acid) or poly(lactic acid)]-poly(alkyleneglycol). Still other injectable particles include a surface which is a copolymer of a poly(lactic acid) or poly(glycolic acid), with two or more moieties of poly(alkyleneglycol). Alternatively, the injectable particle can include as its surface a copolymer of a poly(lactic-co-glycolic acid), poly(lactic acid), or poly (glycolic acid) with poly(alkyleneglycol), wherein the copolymer is blended with poly(lactic-co-glycolic acid). Other useful coatings will be apparent to those of skill in the art.

Modification of Particle Surface Properties

The poly(alkyleneglycol) can also be used with or replaced by a compound that affects the charge or lipophilicity or hydrophilicity of the particle. For example, a polymer other than poly(alkyleneglycol) is used in addition to or instead of poly(ethyleneglycol) as the surface hydrophilic coating. Any biocompatible hydrophilic polymer can be used for this purpose, including but not limited to poly(vinyl alcohol). The particle can also be coated with a dextran, which are in general more hydrophilic than poly (alkyleneglycol) but less flexible. Particles coated with dextran are known in the art. For example, dextran coated nanoparticles have been used for magnetic resonance imaging (MRI). See, for example, U.S. Pat. No. 5,766,572, issued to Hasegawa et al,. on Jun. 16, 1998.

Poly(alkyleneglycol) (which can also be referred to as a poly(alkyleneoxide), if the polymer was prepared from an oxide instead of a glycol) is employed as a polymer constituent, such as a block of a block copolymer. As used herein, the term poly(alkyleneglycol) refers to a polymer of the formula HO-[(alkyl)O][y]-OH, wherein alkyl refers to a $C_1$ to $C_4$ straight or branched chain alkyl moiety, including but not limited to methyl, ethyl, propyl, isopropyl, butyl, and isobutyl. Y is an integer greater than 4, and typically between 8 and 500, and more preferably between 40 and 500. In vivo results show that the higher the molecular weight (MW) of PEG, the longer the circulation time in the blood (the half-life). See, U.S. Pat. No. 5,543,158, to Gref et al. Thus, the in vivo half-life of the particles can be controlled by varying the size of the poly(ethyleneglycol).

Specific examples of poly(alkyleneglycol) include poly (ethyleneglycol), polypropylene 1,2-glycol poly(propylene oxide), and polypropylene 1,3-glycol. A preferred hydrophilic polymeric moiety is PEG of a molecular weight of approximately 5,000 Da. Other hydrophilic polymers that can be used in place of poly(alkyleneglycol) are polypyrrolidone, dextrans, and poly(vinyl alcohol) with a different percent acetyl content. A suitable commercial product is Pluronic F68 (BASF Corporation), a copolymer of polyoxyethylene and polyoxypropylene, which is approved by the U.S. Food and Drug Administration (FDA).

Particulate Contrast Agent Pharmaceuticals

In a third aspect, the present invention provides a pharmaceutical formulation comprising:

a radiopaque particle comprising:

(a) a radiopaque core, with the proviso that the core is not an iron oxide;

(b) an organic layer substantially surrounding the core; and (c) a pharmaceutically acceptable sterile carrier.

The above discussion is generally applicable to this aspect of the invention. In preferred embodiments, the core is an organic, preferably iodinated contrast agent. In other preferred embodiments, the core is an inorganic iodide such as cesium iodide or, alternatively a metal in its (0) oxidation state. Presently preferred metals include, Cu(0), Ni(0), Pd(0), Pt(0), Au(0), Ag(0) and combinations thereof. The metal core can be magnetically active (e.g., paramagnetic, superparamagnetic, etc.), however, in a preferred embodiment, the metal core is not superparamagnetic.

As discussed above, preferred organic coatings are those which will enable the particle to escape rapid phagotization by the RES of the subject. Suitable organic coatings include poly(ethyleneglycol), glucouronic acid, sialic acid, combinations of these groups and polymers of one or more than one of these groups. When polymers of these groups are utilized, they can be copolymers formed between these and other groups.

Suitable carriers are well known in the art and the choice of an appropriate carrier is within the abilities of one of skill in the art. Typically, the administration of contrast media for imaging tumors or other disease states is parenteral, e.g., intravenously, intraarterially or subcutaneously. Thus, in a preferred embodiment, the invention provides compositions for parenteral administration which comprise a solution of contrast media dissolved or suspended in an acceptable carrier, preferably an aqueous carrier. The concentration of particles varies depending on the radiopacity of the contrast agent but typically varies from 0.1 μmol/kg to 100 μmol/kg. A variety of aqueous carriers may be used, e.g., water, buffered water, 0.9% saline, 0.3% glycine, hyaluronic acid and the like. A presently preferred carrier is normal saline.

These compositions can be sterilized by conventional, well known sterilization techniques. Alternatively, certain presently preferred particles can be sterile filtered. As certain preferred particles of the invention can be below the 0.2 or 0.4 micron cutoffs of commercially available sterile filtration devices, these particles will pass through the filter.

It is generally to be desired that the particles of the invention remain within the blood pool for a time sufficient to allow the imaging experiment to be completed. In a preferred embodiment, the particle is substantially unphagocytized by cells of the reticuloendothelial system for a time period of from about 5 minutes to about 3 hours following injection of the particle into an animal.

The aqueous particle solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Although particles of a wide range of sizes can be used in the present invention, certain particle sizes are presently preferred. Thus, in a preferred embodiment, the selected particle size is from about 1 nanometers to about 1 microns in diameter, more preferably from about 5 nanometers to about 500 nanometers in diameter, more preferably still, from about 10 nanometers to about 60 nanometers in diameter.

Data Acquisition

In another preferred embodiment, the method of the invention further comprises measuring a series of x-ray absorptions by the tissue of interest (e.g., a tumor) over a selected time period. The discussion which follows exemplifies one such embodiment.

Also embodied in this invention is a method for using CT x-ray absorption measurements in conjunction with particulate contrast agents to image tumors and characterize their microvessels accordingly. The system is based on an algorithm used to assign grey scale values according to the microvascular permeability values or the fractional blood volume (fBV) to the imaging elements of the tissue of interest. A comparison of the grey scale image and numerical values of $K^{PC}$ and fBV is made to previously obtained image-controls which were already correlated with histopathologic grades of, for example, a lesion. In this manner, the image of the lesion is used to determine the histopathologic grade of the lesion without histological examination.

Other instruments and imaging parameters which can be used in the method of the invention will be apparent to those of skill in the art.

A subject/patient referred for assessment of tissue microvascular status is positioned on the patient table of a computed tomography (CT) unit, for example, the helical CT scanner manufactured by General Electric. In advance of the CT examination, an intravenous catheter, such as an 18-gauge angio-catheter, will have been placed in an antiorcubital vein for purposes of intravenous administration of the particulate contrast agent. Prior to the injection of contrast medium, it may be elected to acquire images of the subject over the anatomic region-of-interest for purposes of localization and to define the position and arrangement of landmarks. After such localization, the CT table will be positioned within the CT scanner so that additional images can be acquired at the selected location of interest for definition of vascular characteristics of a suspected lesion. A representative tissue, site and lesion might be the prostate gland located within the pelvis for purposes of defining vascular status in a prostatic tumor mass.

A series of CT images is acquired with appropriate temporal resolution beginning just prior to contrast medium administration and continuing through the period of contrast administration (5–30 seconds) and for a selected time period after the administration. A wide range of image acquisition periods can be used in the method of the invention.

In a preferred embodiment, the selected time period is from about 10 seconds postcontrast to about 5 hours postcontrast, more preferably from about 30 seconds postcontrast to about 1 hour postcontrast, more preferably still from about 1 minute postcontrast to about 10 minutes postcontrast.

A typical series might include an image every five seconds before and during the contrast medium administration, slowing further to an image every ten seconds for the subsequent three minutes, and finally slowing to an image every 30 seconds until the 10 minute completion of the series. These serial images are used to generate the dynamic enhancement data from the tissue and from the blood as measured in a vessel to be used for kinetic modeling and, ultimately, to the calculation of blood volume and endothelial permeability within the tissue of interest. After the completion of the dynamic 10 minute acquisition localized to the region-of-interest, it may be elected to acquire additional CT images of the patient in other anatomic sites to extract additional diagnostic data or for delayed images in the same site. After CT scanning, the subject is removed from the scanner unit, the intravenous catheter can be removed and the patient allowed to leave the area. The data acquired from the CT imaging procedure is processed to provide the necessary information Data Processing In a presently preferred embodiment, the method of the invention processes the data set acquired from the CT imaging by a method comprising at least one algorithm.

A variety of algorithms can be used to practice the present invention. In a presently preferred embodiment, the algorithm is a linear regression analysis of the slope of the permeability of a particulate contrast media in tissue. In a presently preferred embodiment, the destination of the contrast medium in the tissue is the intravascular space and an extravascular space of that tissue.

Postprocessing of the imaging data will include measurement of the serial changes in enhancement (typically measured in Hounsfield units) within the regions-of-interest defined by the operator at the CT console. In addition to a region-of-interest defined in the tissue, the operator will define a second region-of-interest within the lumen of a large vascular structure such as the vena cava. The dynamic changes in CT number, both within the tissue of interest and for the venous blood, will be plotted over the 10 minute dynamic acquisition period. With computer assistance, the dynamic CT data will be fit to a 2-compartment kinetic model representing the intravascular and extravascular interstitial compartments. The fractional blood volume, fBV, and the co-efficient of permeability surface area product, $K^{PS}$, can then be calculated. These parameters, fBV and $K^{PS}$, will be used to characterize tissue vascularity and may be helpful in individual subjects to differentiate normal from abnormal tissues and, further, to define tissue angiogenic status and tumor grade in the case of malignancies. The contrast enhanced CT images can also be used to define the location, caliber, and flow characteristics of vascular structures within the scanned anatomic regions. Moreover, the images can be utilized to monitor the effect of potentially therapeutic drugs which are expected to alter microvascular status.

In one exemplary embodiment, the tissue can also contain a region having a tumor or other tissue insult. In general, if the enhancement slope is greater in the tissue than a predetermined reference value, a pathological condition is implied, including but not limited to, the presence of a tumor in the imaged tissue. In addition to a difference in slope, the degree of difference in the enhancement slopes is proportional to the degree of malignancy or pathology in the tissue. To create a model that indicates the degree of malignancy, the enhancement slopes are analyzed and a null hypothesis of no difference in the slopes is assumed. If the null hypothesis is rejected, the reciprocal of the confidence level is calculated and presented as a simple grey scale superimposed on the image. Thus, the more unlikely the null hypothesis (i.e., the more malignant the tumor) in a given pixel or group of pixels, the more intense the brightness assigned to that pixel.

To determine the microvascular permeability of a tumor, a kinetic model of microvessel "leakiness" is generated. Curve fitting algorithms are used to find the change in x-ray absorption of the imaged tissues before and after particle administration. For example, in CT imaging, from the change in contrast, parameters important to determining the microvascular permeability are determined. Precontrast values for normal tissue and tissues of interest are obtained. Postcontrast absorption values are calculated based on signal intensity. The precontrast absorption value for each response is then subtracted from the postcontrast value to obtain the change in the tissue x-ray absorption, at all postcontrast time points. The change in intensity is taken to be directly proportional to the local particle concentration in a tissue.

In CT imaging, the functional characteristics, fractional blood volume (fBV), fractional leak rate (FLR), fractional reflux rate (FRR), and permeability surface area product (PS), which is directly related to the microvascular permeability, are estimated from the absorption data by kinetic analysis.

The method described above is useful with substantially any tissue type. In a preferred embodiment, the tissue is a member selected from the group consisting of normal tissue, diseased tissue and combinations thereof. In a further preferred embodiment, the tissue is at least partially a diseased tissue and the diseased tissue is a member selected from the group consisting of tissues which are neoplastic, ischemic, hyperplastic, dysplastic, inflamed, traumatized, infarcted, necrotic, infected, healing and combinations thereof.

An exemplary tissue model is the tumor model. The tumor model is composed of three compartments, tumor cells, tumor blood (B) and tumor extracellular fluid (ECF). The kinetics of fractional transport of MCM from B to ECF is designated the FLR and from ECF to B as FRR. As described above, the leakiness of the tumor microvasculature allows particles to accumulate in the extracellular fluid of the tumor. The fractional plasma volume (fPV) of the tumor is a proportionality constant, determined by the size of the tumor. With knowledge of the hematocrit, fPV and fBV are easily interconverted.

In one embodiment, four parameters of the model (k, IC, FLR, FRR and fPV) are fitted to the image intensity data from the IVC and from the tumor using the SAAM II program (SAAM Institute, Seattle Wash.). In another, more preferred embodiment, a linear regression analysis is used to compare the slopes of tissue and blood responses to radiopaque particles to determine microvascular permeability.

Microvascular permeability can be estimated as the product of fPV (or fBV after correction for hematocrit to yield an estimate of the plasma volume of the tissue) and FLR.

Various different statistical analyses can be done to correlate the microvascular permeability results obtained by imaging to the histological results obtained by pathologic analysis, i.e., a high microvascular permeability value is indicative of malignancy and a low microvascular permeability value is indicative of benign status. A preferred method is the two-tail, paired t-test. For this analysis, a correlation value of greater than 0.70, preferably greater than 0.80 with a probability of correlation of preferably less than 0.05 is assigned statistically significant.

In one preferred embodiment, the property determined by the method of the invention is a tissue vascular volume. In another preferred embodiment, the property determined by the method of the invention is a coefficient of microvascular permeability surface area product.

In a further preferred embodiment, the property determined by the method of the invention is a property of a tissue in which the intravascular space and the extravascular interstitial space are joined communicatively and the property is a rate of transfer of the agent from the intravascular space into the extravascular interstitial space.

Systems and Kits

It is anticipated that the method and the particles of the invention can be incorporated into a commercial kit or system for characterizing vessels in any tissue and for grading certain types of tumors. Moreover, the method and particles of the invention can be incorporated into a kit for determining the changes in tissue microvascular characteristics in response to treatment measures.

The kit would incorporate a system wherein an algorithm is used to assign a grey scale to the regions of interest from the permeability values collected from the imaging. The grey scale values could be combined to form an image wherein the regions of interest which accumulated the most particulate contrast agent would appear the brightest. The combined grey scale image could then be compared to previously obtained controls that had been correlated with histopathologic grade to grade the tumor being imaged.

In a preferred embodiment, the algorithm performs a simple linear regression analysis. The data analyzed are the slopes of response of both tissue and blood to particulate contrast agent. In other words, the permeability over time is plotted. The slope of the permeability of the tissue is compared to the slope of the permeability of blood. If the slopes are the same, the tissue is not more permeable to particles than normal tissue and likely is not pathogenic. If the slope is greater than the slope of normal tissue, the degree of difference is proportional to the degree of pathology. A simple statistical analysis can then be done, assuming that the null hypothesis is no difference in slopes, to determine the confidence level of the analysis. If the null hypothesis is rejected because p<0.05, the reciprocal of this p value can be calculated and presented as a simple grey scale superimposed on the image. Thus, the more unlikely the null hypothesis in a given pixel or group of pixels, the brighter the pixel or group of pixels.

In addition to the algorithm and instructions for use, the kit may contain particles needed to enhance the contrast of the tumor and may further contain directions on the administration and use of the particles in conjunction with the algorithm.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for determining a property of a tissue extracellular space comprising an intravascular space and an extravascular space, said method comprising:

(a) delivering to a tissue intravascular space a particulate radiopaque agent, wherein said agent is not substantially phagocytized by cells of the reticuloendothelial system during at least a selected time period;

(b) allowing said agent to distribute between said intravascular space and said extravascular interstitial space for said selected time period, wherein at least a portion of said particulate radiopaque agent distributes into said extravascular interstitial space during said selected time period, thereby forming a distribution of said agent;

(c) measuring said distribution of said agent by obtaining at least one x-ray absorption data set of a region encompassing said extravascular interstitial space; and (d) determining said property from said data set.

2. The method according to claim 1, wherein said agent is nonmagnetic and nonferrous.

3. The method according to claim 1, wherein said method further comprises measuring a series of x-ray absorption data sets of said tissue vascular space over a time period comprising said selected time period.

4. The method according to claim 1, wherein said data set is processed by a method comprising at least one algorithm.

5. The method according to claim 1, wherein said property is a tissue vascular volume.

6. The method according to claim 1, wherein said property is a microvascular permeability.

7. The method according to claim 1, wherein said intravascular space and said extravascular interstitial space are joined communicatively and said property is a rate of transfer of said agent from said intravascular space into said extravascular space.

8. The method according to claim 1, wherein said selected particle size is from about 1 nanometers to about 1 micron in diameter.

9. The method according to claim 8, wherein said selected particle size is from about 5 nanometers to about 500 nanometers in diameter.

10. The method according to claim 9, wherein said selected particle size is from about 10 nanometers to about 60 nanometers in diameter.

11. The method according to claim 1, wherein said selected time period is from about 10 seconds postcontrast to about 5 hours postcontrast.

12. The method according to claim 11, wherein said selected time period is from about 30 seconds postcontrast to about 1 hour postcontrast.

13. The method according to claim 12, wherein said selected time period is from about 1 minute postcontrast to about 10 minutes postcontrast.

14. The method according to claim 1, wherein said tissue is a member selected from the group consisting of normal tissue, diseased tissue, traumatized tissue and combinations thereof.

15. The method according to claim 14, wherein said diseased tissue is a member selected from the group consisting of tissues which are neoplastic, ischemic, hyperplastic, dysplastic, inflamed, traumatized, infarcted, necrotic, infected, healing and combinations thereof.

16. The method according to claim 1, wherein said agent is a member selected from the group consisting of liposomes, emulsions, inorganic particles, organic particle, mixed organic-inorganic particles and combinations thereof.

17. The method according to claim 16, wherein said agent comprises an organic iodinated radiopaque agent.

18. The method according to claim 16, wherein said agent comprises an inorganic core substantially surrounded by an organic coating.

19. The method according to claim 18, wherein said inorganic core is a metal in its (0) oxidation state.

20. The method according to claim 18, wherein said inorganic core is cesium iodide (CsI).

21. The method according to claim 18, wherein said organic coating is a member selected from the group consisting of polysaccharides, polyethers and combinations thereof.

22. The method according to claim 21, wherein said organic coating is a member selected from the group consisting of poly(ethyleneglycol), sialic acid, glucouronic acid, dextran, hydroxyethylstarch and combinations thereof.

* * * * *